Figure 1:
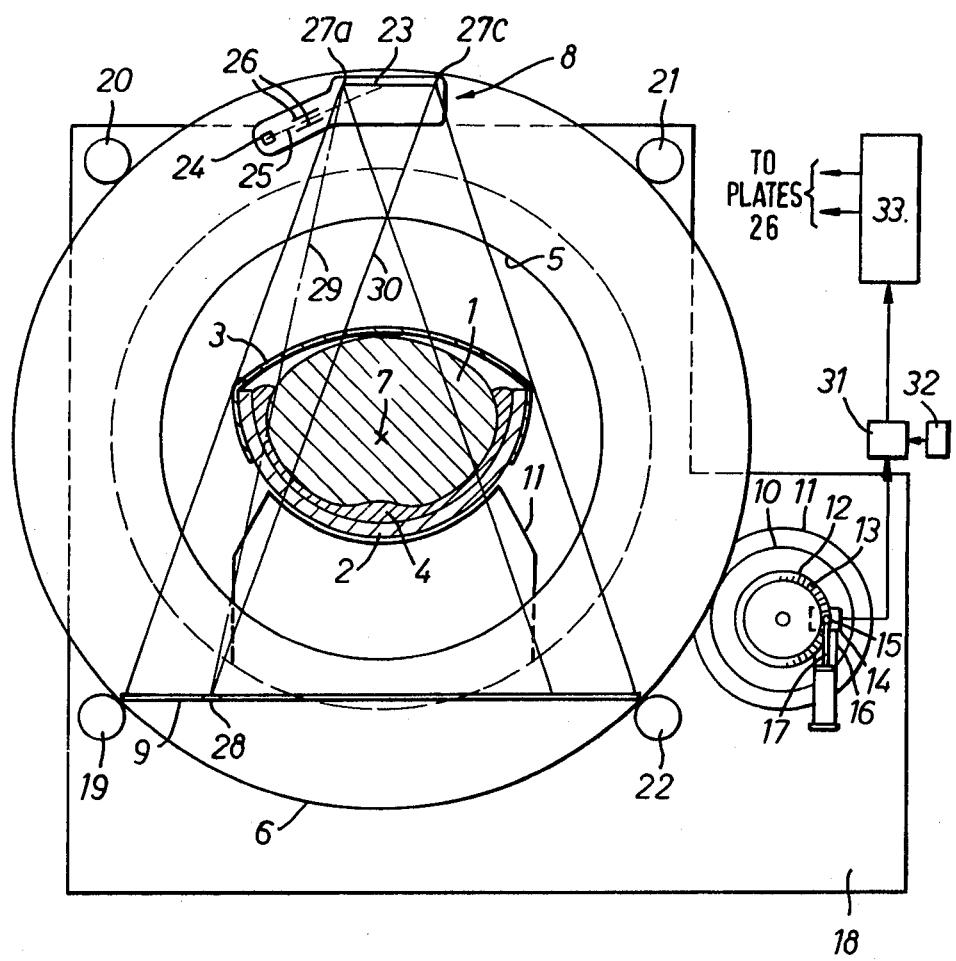

United States Patent [19]

Froggatt

[11] 4,081,681
[45] Mar. 28, 1978

[54] TREATMENT OF ABSORPTION ERRORS IN COMPUTERIZED TOMOGRAPHY

[75] Inventor: Robert Justin Froggatt, Southall, England

[73] Assignee: EMI Limited, Hayes, England

[21] Appl. No.: 755,629

[22] Filed: Dec. 30, 1976

[30] Foreign Application Priority Data

Jan. 15, 1976 United Kingdom ............... 1497/76

[51] Int. Cl.$^2$ ............... A61B 6/02; G01N 23/08; H05G 1/30
[52] U.S. Cl. ............................. 250/360; 250/445 T
[58] Field of Search ............................. 250/360, 445 T

[56] References Cited

U.S. PATENT DOCUMENTS 3,937,965  2/1976  Vasseur .......................... 250/445 T Primary Examiner—Davis L. Willis
Assistant Examiner—T. N. Grigsby
Attorney, Agent, or Firm—Cooper, Dunham, Clark, Griffin & Moran

[57] ABSTRACT

A computerized tomographic apparatus is disclosed, as well as a method of operating such apparatus. In circumstances where collimation between the body under examination and the radiation-sensitive detector means is difficult to apply, errors in evaluated absorption coefficients for locations distributed over a cross-sectional slice of the body due to scatter within the slice are reduced by producing a first estimate of the distribution of said absorption coefficients, using this estimate to obtain an indication of the amount of scatter likely to arise from the various locations when irradiated along different paths and using such indication to effect scatter compensation.

13 Claims, 2 Drawing Figures

TREATMENT OF ABSORPTION ERRORS IN COMPUTERIZED TOMOGRAPHY

The present invention relates to radiography and it relates especially, though not exclusively, to that branch of radiography which has become known as computerised axial tomography, or briefly C.A.T. An apparatus capable of performing C.A.T. ascertains the absorption suffered by penetrating radiation, such as X-radiation, on traversing a plurality of substantially linear paths through a crosssectional slice of the body. The absorption values so ascertained are processed to evaluate the absorption (or transmission) coefficient with respect to said radiation at each of a plurality of elemental areas distributed over the slice. Such an apparatus is described in U.S. Pat. No. 3778614.

It has been usual hitherto to ascertain the aforementioned absorption values by detector means, including one or more collimated detector devices; the collimation being effected to prevent, so far as is practicable, the detection of scattered radiation. In these arrangements, the measurement of absorption of radiation along the various paths is typically effected by scanning the detector means mechanically with respect to the body. The scanning typically involves lateral and rotational scanning movements.

However it has recently been proposed, for example in U.S. Application Nos. 608276 now U.S. Pat. No. 4,002,917, 630779 now U.S. Pat. No. 4,010,370 and 733941 that a source of X-radiation be rapidly scanned laterally relative to the body by electrical or electromagnetic deflection of a beam of electrons over an X-ray emitting target. When such rapid lateral scanning of the source is employed, it is inconvenient and practically difficult to cause the detector means to follow the movement, and it has therefore been the practice to use a fixed bank of detector devices relative to which the source is scanned. In the interest of rapid data acquisition, the source of radiation is arranged to produce a fanlike substantially planar spread of radiation which overlaps a substantial number of the detector devices. This means, however, that some of the detector devices, particularly those in the centre of the array, are irradiated whilst the source is scanned over a substantial range of positions and thus, if collimators are used, they must be wide enough to accept radiation from all positions in said range. The widening of the collimators, however, can permit in some circumstances the detection of more scattered radiation than is acceptable, and also gives rise to practical problems in that the collimator for one detector device tends to intercept radiation which should be collected by neighbouring detector devices.

It is an object of this invention to reduce the difficulties and the apparently conflicting requirements imposed by the foregoing considerations.

According to the invention there is provided radiographic apparatus including a source of penetrating radiation, such as X-radiation, arranged to project radiation through a cross-sectional slice of a body, detector means disposed to receive radiation emergent from the body and processing means for operating on output signals, provided by said detector means and indicative of the absorption suffered by said radiation on traversing substantially linear paths through said slice, to evaluate absorption coefficients for a plurality of elemental areas distributed over said slice, said processing means including compensating means for adjusting said evaluated coefficients to allow for the detection, by said detector means, of scattered radiation.

Figure 2:
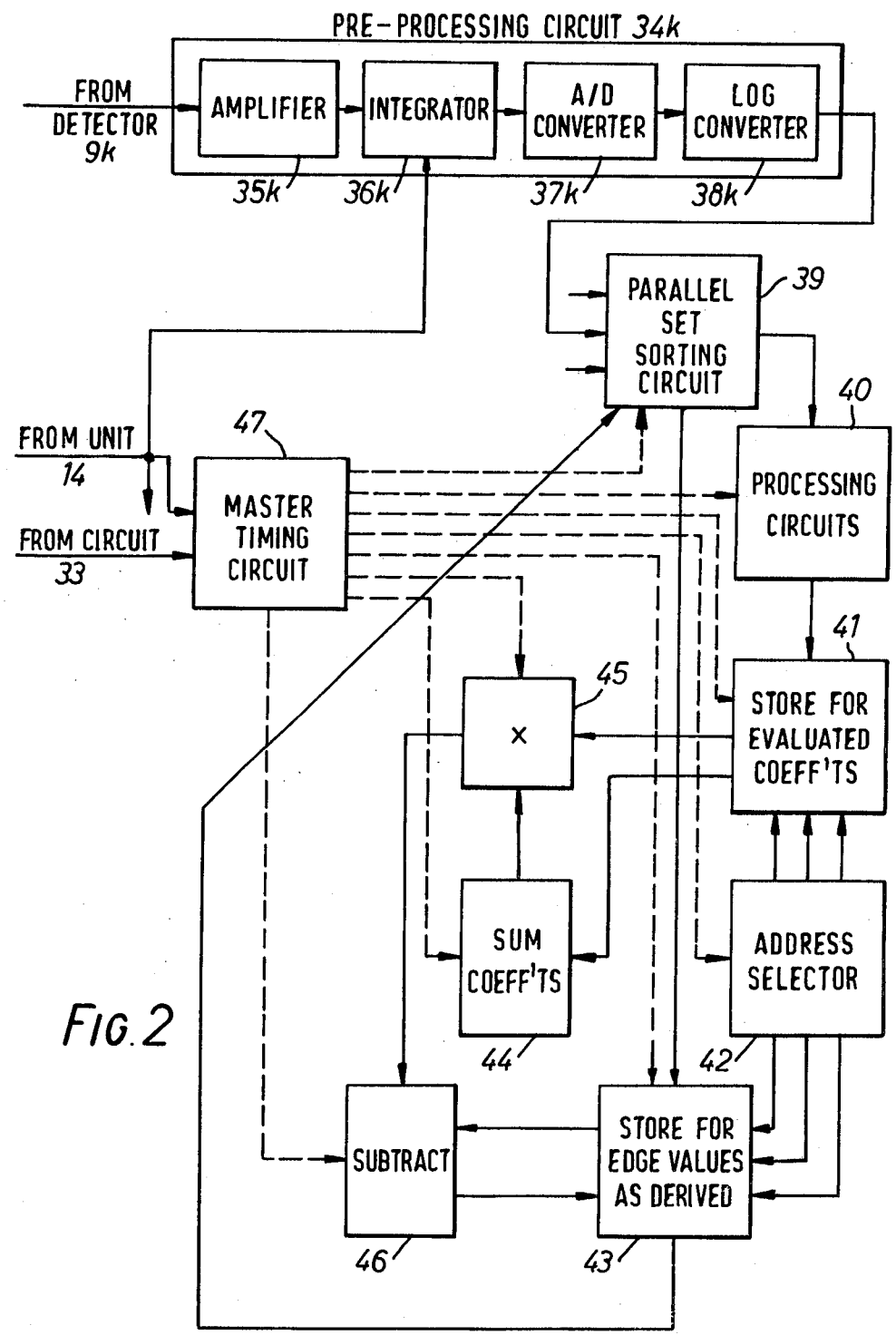

In order that the invention may be clearly understood and readily carried into effect, one embodiment thereof will now be described, by way of example only, with reference to the accompanying drawings of which:

FIG. 1 shows, in front elevational view, part of an apparatus which incorporates one example of the invention, and FIG. 2 shows, in flow diagram form, a manner in which coefficients assigned to elemental areas can be compensated for the effects of scatter.

Referring now to FIG. 1, a body 1 to be examined is supported supine on a semi-cylindrical couch 2 of unitary construction, and is secured to the couch 2 by means of one or more straps 3 which are secured to the outside of the bed 2 as shown. Both the bed and the strap are made of material which is substantially transparent to X-radiation, and a suitable packing material 4 having an absorption similar to that of the body 1 is disposed in gaps between the body 1 and the couch 2 in order that the body is not surrounded by a layer of air, which exhibits markedly different absorption to X-radiation to human tissue. Suitable packing material is water in a flexible bag, or alternatively viscous or particulate material in one or more flexible bags can be used.

The part of the body 1 which is of interest is located in an aperture 5 in a turntable member 6 which is arranged to rotate around the body 1 about an axis 7 which extends perpendicularly to the plane of the paper (i.e. a horizontal axis in practice). The turntable member 6 carries an X-ray source 8 and array 9 of radiation detectors, and the member 6 and its attachments are rotated by means of a gear wheel 10 driven by an electric motor 11. The wheel 10 engages teeth (not shown) formed all around the periphery of member 6. The detectors 9 can be of any suitable kind, for example scintillation crystals with associated photomultipliers, scintillation crystals with associated photodiodes etc.

The spindle of motor 11 carries a disc 12 which is formed with an annular graticule 13. The graticule cooperates with a photocell 14 and an associated light source 15 in a known manner to produce signal pulses which are indicative of the progress of the rotation of turntable member 6. Photocell 14 and the light source 15 are mounted on respective brackets 16 and 17 which are secured to a main frame 18 for the apparatus which frame also supports the motor 11. It will be appreciated that the turntable member 6 will also require support and location and this is provided by suitable idler wheels 19, 20, 21 and 22 mounted on the frame 18. The form of the frame 18 is not of the essence of this invention and it is shown in the particular form of FIG. 1 for the purposes of example only.

The source 8 includes an elongated target/anode structure 23, an electron gun 24, which produces a beam 25 of electrons, and deflection plates 26, although deflection coils could equally well be used. Two extreme source positions 27a and 27c are shown in FIG. 1, from which it can be seen that, in any source position, a fan of radiation is directed at the body 1. It can also be seen that the detector array 9 takes no part in the lateral movement, this array being of sufficient breadth to accommodate the scanning of the radiation.

It will be appreciated that some detectors, for example the one shown at 28, need to be capable of receiving radiation from a number of different directions, for example as shown by the beams 29 and 30 which relate to source positions 27a and 27c respectively. This would cause difficulties, as mentioned previously, if the detectors were collimated and so, in this example, no collimators are used and the effects of scatter are allowed for by suitable computation as will be made clear later.

The output signal pulses derived from the photocell 14 are applied to a timing pulse shaping circuit 31, which also receives start and stop command pulses from a remote control switch 32. The shaped pulses from circuit 31 are fed to a timing circuit 33 which is arranged to generate deflection waveforms for application to the deflection plates 26 of tube 8 so that the lateral scanning of the radiation is suitably synchronised with the rotation of turntable member 15, in accordance with a desired inter-relationship between the lateral and rotational scanning movements. Suitable inter-relationships between the two scanning movements are described in the aforementioned U.S. applications No. 630779 and 722941 and, as such inter-relationships are not essential to the understanding of this invention, they will not be further described herein.

The signals provided by the detector array 9 during the scanning are converted into discrete signals indicative of the amounts of radiation emergent from the body along respective, substantially linear paths, by causing the detectors to feed respective integrator circuits which are read and reset periodically under the influence of the timing pulses derived from the photocell unit 14. These discrete signals are digitised, converted to logarithmic form, and processed in any convenient manner, such as that described in the aforementioned U.S. Pat. No. 3778614 or that described in U.S. Pat. No. 3924129, allowance being made for the fact that the beam paths followed by the radiation through the body will not be strictly linear because of the effects of the steady rotation of turntable member 6.

Referring now to FIG. 2, the processing arrangement utilised in accordance with this example of the invention will be described in more detail. Each detector in the array 9 feeds a respective pre-processing circuit 34; only the circuit 34 for the k'th detector being shown in FIG. 2. Each circuit 34 includes an amplifier 35, an integrator 36 which, as mentioned previously, is periodically read and reset by timing pulses derived from the photocell unit 14, an analogue-to-digital converter circuit 37 and a logarithmic converter circuit 38. All of the preprocessing circuits 34 feed a common parallel set sorting circuit 39 which is effective in the manner disclosed in U.S. Application No. 544799 to sort the output signals, which are commonly referred to as "edge values", into sets relating to substantially parallel beam paths through the body. The sorted edge values are applied, parallel set after parallel set, to a processing circuit 40 of the kind described in the aforementioned U.S. Pat. No. 3924129. Alternatively, the processing arrangements disclosed in U.S. Pat. No. 3778614 can be used, in which case the circuit 39 is not required.

The circuit 40 is effective to evaluate, from the edge value data applied thereto, an absorption coefficient for each of many elemental areas distributed over the irradiated cross-sectional slice of the body. If the detectors 9 had been suitably collimated, this evaluation would have been the final step in the examination, but since the detectors are not collimated, further processing is required to reduce or eliminate the effects of scatter. This further processing involves the components 41 through 46, which will now be described in more detail.

The evaluated coefficients are applied to a random access digital store 41 which contains a storage location for each of the aforementioned elemental areas. Typically the areas are notionally delineated in the form of a rectangular matrix in the irradiated slice of the body, and it is desirable that the storage locations of store 41 be arranged in similar format.

In order to compensate the evaluated coeffcents for the effects of scatter, each elemental area must be considered as a potential scattering centre for each beam path which intersects it. It is clear that it is necessary to ascertain the effects of scatter for any beam path and elemental area only for edge values which are obtained at the same time as the edge value relating to the beam path in question. An address selector 42 is arranged to designate the linear (or substantially linear) combination of elemental areas interesected by a first beam path. It also designates a first elemental area on said first beam path. The interconnection of address selector 42 with the digital store 41 is such that, once the first beam path and elemental area in question have been designated by selector 42, the coefficients evaluated for all other elemental areas intersected by the said first beam path from the irradiated side of the body up to said first designated elemental area are applied, in any sequence, to a summing circuit 44 which thereby evaluates the absorption likely to have been suffered by the radiation on traversing said first beam path through said body as far as said first designated elemental area. This evaluated absorption is applied to a multiplying circuit 45, and the evaluated absorption coefficient for the first designated elemental area is also applied to circuit 45 from store 41 in response to a signal applied thereto from the address selector 42. These two values when multiplied together provide an indication of the amount of scattered radiation likely to have been produced by the projection of radiation through said first designated elemental area along said first designated beam path. This scatter value is assumed to be isotropic, and thus has to be subtracted from the other edge values which were derived at the same time as the edge value relating to said first designated beam path. The aforementioned subtraction is effected by means of a substraction circuit 46, to which the output signals from circuit 45 are applied, and a second digital store 43 which is arranged to store all the edge values in the order in which they were derived. In response to signals from the address selector 42, store 43 applies, in sequence, to circuit 46 all the edge values, apart from the one relating to said first designated beam path, which relate to beam paths irradiated at the same time as said first designated beam path. The corrected edge values are re-inserted in the appropriate locations of store 43, and the address selector circuits are then arranged to designate a second elemental area on said first beam path. The above process is repeated until all elemental areas along the first beam path have been dealt with, and a second beam path is then designated. The procedure is repeated until all combinations of beam paths and elemental areas have been dealt with, at which time the store 43 holds a complete set of scatter compensated edge values. These compensated edge values are then applied, via circuit 39, to the processing circuit 40 and an improved evaluation of the various absorption coefficients, duly compensated for scatter, is produced.

The above sequence of events can, of course, be repeated if desired in order to successively approximate the true values for the coefficients.

All of the functions performed by the components 39 to 46 inclusive are carried out under the control of a master timing circuit 47, as indicated by the respective interconnections, shown in dashed lines for clarity, between the circuit 47 and the components 39 to 46. Circuit 47 receives input information from unit 14 and circuit 33 and this enables the derivation of the data to be accurately monitored, so that all beam paths can be properly identified.

What I claimed is:

1. Radiographic apparatus including a source of penetrating radiation such as X-radiation, arranged to project radiation through a cross-sectional slice of a body, detector means disposed to receive radiation emergent from the body, said detector means providing output signals indicative of the absorption suffered by said radiation on traversing substantially linear paths through said slice, and processing means for operating on said output signals to evaluate absorption coefficients for a plurality of elemental areas distributed over said slice, said processing means including compensating means for adjusting said so evaluated absorption coefficients to compensate for the detection, by said detector means, of scattered radiation.

2. Apparatus according to claim 1 wherein said compensating means comprises means for deriving respective scatter adjustment signals for the elemental areas intersected by the path giving rise to a given output signal, and means for combining the scatter adjustment signals relating to said given output signal with other output signals which correspond to radiation received by the detector means at substantially the same time as the radiation corresponding to said given output signal to compensate said other output signals for scatter due to matter disposed at the said elemental areas along the beam path to which said given output signal relates.

3. Apparatus according to claim 2 including a store for said evaluated coefficients, and wherein said means for deriving said respective scatter adjustment signals comprises means for summing the stored evaluated coefficients relating to elemental areas traversed by the radiation to reach a given one of said elemental areas along said beam path to which said given output signal relates to provide thereby a sum signal, and means for multiplying the sum signal by the evaluated coefficient stored for said given area to produce a scatter adjustment signal in respect of said given area.

4. Apparatus according to claim 2 wherein said means for combining comprises a subtraction circuit for subtracting, from each of said other output signals, the scatter adjustment signal for each area along said path to which said given output signal relates, to produce thereby scatter compensated output signals.

5. Apparatus according to claim 2 including means for designating each output signal in turn as said given output signal to produce modified output signals each containing multiple scatter adjustments.

6. Apparatus according to claim 5 including means for processing said modified output signals to evaluate scatter compensated absorption coefficients for said elemental areas.

7. Apparatus according to claim 6 wherein said means for processing said modified output signals and said processing means for operating on said first mentioned output signals operate in accordance with substantially the same processing technique.

8. Apparatus according to claim 7 wherein said means for processing said modified output signals and said processing means for operating upon said first mentioned output signals are constituted by a common processing means.

9. Radiographic apparatus including means for processing electrical signals indicative of penetrating radiation, such as X-radiation, emergent from a patient position along sets of substantially linear beam paths to evaluate absorption coefficients at each of a plurality of locations distributed over a region of said patient position, means for evaluating a scatter signal, in respect of each location along each beam path, which is indicative of the extent to which each location scatters said radiation, means for modifying each electrical signal by correcting said signal in accordance with all of the scatter signals evaluated in respect of locations traversed for the other output signals relating te beam paths in the same set as the path to which the output signals being modified relates, and means for processing the modified signals in substantially the same manner as that in which said first mentioned electrical signals were processed to evaluate scatter compensated absorption coeficients for said locations.

10. Apparatus as in claim 9 wherein each of said sets of paths comprises paths along which said penetrating radiation propagates substantially concurrently.

11. A method of examining a crosssectional slice of a body by means of penetrating radiation such as X-radiation including the steps of:
  (a) obtaining electrical signals indicative of the absorption suffered by said radiation on traversing each path of a plurality of sets of substantially linear paths through said slice,
  (b) processing said electrical signals to provide absorption coefficient values, with respect to said radiation, at each of a plurality of locations distributed over said slice,
  (c) evaluating for each location and for each path passing therethrough, a scatter signal indicative of the extent to which each location scatters radiation incident thereon along each said path traversing it,
  (d) modifying each electrical signal by correcting the signal in accordance with the scatter signals evaluated in respect of all locations traversed by other paths in the same set as the path to which the signal being modified relates, and
  (e) processing, by the same technique as was used in step (b), the modified signals to provide scatter compensated values of absorption coefficient for said locations.

12. A method as in claim 11 wherein each of said sets of paths comprises paths along which said penetrating radiation propagates substantially concurrently.

13. A medical diagnostic X-ray machine for examining a slice of a patient which extends along a planar section through the patient, comprising:
  means for generating X-radiation propagating through the patient from locations distributed along an orbit extending at least half way around the patient, said X-radiation propagating along a set of beam paths which pass through the patient along said section, and means for producing a corresponding first set of beam value signals each related to the amount of X-radiation which has passed through the patient along a respective one of said beam paths, wherein the patient slice is divided into a multiplicity of slice elements by a finite Cartesian matrix notionally superimposed on the slice and a number of different beam paths of said set pass through each slice element, the total number of beam paths in the set and the total number of beam value signals in the first set being sufficient relative to the number of slice elements for forming a picture of the slice based on the beam value signals of said first set;

means for deriving first picture elements signals determined by the beam value signals of said first set, each first picture element signal approximating the absorption of the X-radiation in a respective one of the slice elements, said first picture element signals being liable to errors related to the actual absorption of the X-radiation in passing through said slice elements;

means for deriving correction factors which are, respectively, functions of said first picture element signals;

means for correcting at least some of the beam value signals of said first set in response to said correction factors to derive a second set of beam value signals the total number of which is also sufficient relative to the number of slice elements for forming a picture of the slice based on the beam value signals of the second set; and means for deriving second picture element signals determined by said second set of beam value signals to the same extent the first picture element signals are determined by said first set of beam value signals, said second picture element signals being corrected at least in part compared with said first picture element signals for said errors related to the actual absorption of the X-radiation in passing through the elements of the patient slice; and means for forming a picture of the slice of the patient defined by said second picture element signals.

* * * * *

UNITED STATES PATENT AND TRADEMARK OFFICE
CERTIFICATE OF CORRECTION

PATENT NO. : 4,081,681
DATED : March 28, 1978
INVENTOR(S) : ROBERT JUSTIN FROGGATT It is certified that error appears in the above-identified patent and that said Letters Patent are hereby corrected as shown below:

Column 1, line 12, delete "crossectional" and insert
-- cross-sectional --.

Column 3, line 21, delete "722,941" and insert -- 733,941 --.

Column 6, line 20, (Claim 9), delete "te" and insert -- to

Column 6, line 21, (Claim 9), delete "signals" and insert
-- signal --.

Column 6, line 25, (Claim 9), delete "coeficients" and insert
-- coefficients --.

Signed and Sealed this

Third Day of April 1979

[SEAL]

Attest:

RUTH C. MASON
Attesting Officer

DONALD W. BANNER
Commissioner of Patents and Trademarks